US 8,725,532 B1

(12) United States Patent
Ringold

(10) Patent No.: US 8,725,532 B1
(45) Date of Patent: May 13, 2014

(54) SYSTEMS AND METHODS FOR MONITORING CONTROLLED SUBSTANCE DISTRIBUTION

(75) Inventor: James Morgan Ringold, Lawrenceville, GA (US)

(73) Assignee: McKesson Financial Holdings (BM)

( * ) Notice: Subject to any disclaimer, the term of this patent is extended or adjusted under 35 U.S.C. 154(b) by 73 days.

(21) Appl. No.: 13/538,377

(22) Filed: Jun. 29, 2012

(51) Int. Cl.
*G06Q 50/22* (2012.01)
*G06F 19/00* (2011.01)

(52) U.S. Cl.
CPC .................................. *G06F 19/32* (2013.01)
USPC .................................................. 705/2; 705/3

(58) Field of Classification Search
CPC ..... G06F 19/32; G06F 19/324; G06F 19/326; G06F 17/60
USPC ........................................................ 705/2, 3
See application file for complete search history.

(56) References Cited

U.S. PATENT DOCUMENTS

| | | |
|---|---|---|
| 5,235,702 A | 8/1993 | Miller |
| 5,359,509 A | 10/1994 | Little et al. |
| 5,544,044 A | 8/1996 | Leatherman |
| 5,550,734 A | 8/1996 | Tarter et al. |
| 5,644,778 A | 7/1997 | Burks et al. |
| 5,704,044 A | 12/1997 | Tarter et al. |
| 5,832,447 A | 11/1998 | Rieker et al. |
| 5,950,169 A | 9/1999 | Borghesi et al. |
| 6,006,242 A | 12/1999 | Poole et al. |
| 6,073,104 A | 6/2000 | Field |
| 6,202,923 B1 | 3/2001 | Boyer et al. |
| 6,208,973 B1 | 3/2001 | Boyer |
| 6,324,516 B1 | 11/2001 | Shults et al. |
| 6,330,546 B1 | 12/2001 | Gopinathan et al. |
| 6,341,265 B1 | 1/2002 | Provost et al. |
| 6,343,271 B1 | 1/2002 | Peterson et al. |
| 6,632,251 B1 | 10/2003 | Rutten et al. |
| 6,650,964 B2 | 11/2003 | Spano et al. |
| 6,671,692 B1 | 12/2003 | Marpe et al. |

(Continued)

FOREIGN PATENT DOCUMENTS

WO 0173652 10/2001

OTHER PUBLICATIONS

Final Office Action for U.S. Appl. No. 12/480,907 mailed Apr. 2, 2013.

(Continued)

*Primary Examiner* — John Pauls
*Assistant Examiner* — Jason Tiedeman
(74) *Attorney, Agent, or Firm* — Sutherland Asbill & Brennan LLP

(57) ABSTRACT

Systems and methods for monitoring controlled substance distribution include receiving a healthcare transaction at a service provider computer. The healthcare transaction may be parsed to determine the healthcare provider submitting the healthcare transaction, the drug being prescribed as part of the healthcare transaction and the class of controlled substance to which the drug being prescribed belongs. Counters associated with total scripts prescribed by the healthcare provider and the class of controlled substance may be incremented upward in view of the healthcare transaction being approved by a claims processor. A current percentage of the class of controlled substances being prescribed can be calculated for the healthcare provider and compared to a threshold percentage for the particular class of controlled substance. If the current percentage violates the threshold percentage, a notification can be sent to a corporate level or management level for the healthcare provider for review.

20 Claims, 5 Drawing Sheets

(56) References Cited

U.S. PATENT DOCUMENTS

| | | | |
|---|---|---|---|
| 6,671,693 | B1 | 12/2003 | Marpe et al. |
| 6,714,918 | B2 | 3/2004 | Deshpande et al. |
| 7,155,397 | B2 | 12/2006 | Alexander et al. |
| 8,099,339 | B1* | 1/2012 | Pinsonneault et al. ......... 705/28 |
| 2001/0041993 | A1 | 11/2001 | Campbell |
| 2001/0047281 | A1 | 11/2001 | Keresman |
| 2002/0029157 | A1 | 3/2002 | Marchosky |
| 2002/0035488 | A1 | 3/2002 | Aquila et al. |
| 2002/0046169 | A1 | 4/2002 | Keresman et al. |
| 2002/0049617 | A1 | 4/2002 | Lencki et al. |
| 2002/0055856 | A1 | 5/2002 | Adams |
| 2002/0065687 | A1 | 5/2002 | Onoue |
| 2002/0120559 | A1 | 8/2002 | O'Mara et al. |
| 2002/0133503 | A1 | 9/2002 | Amar et al. |
| 2002/0138155 | A1 | 9/2002 | Bristol |
| 2002/0143434 | A1 | 10/2002 | Greeven et al. |
| 2003/0050803 | A1 | 3/2003 | Marchosky |
| 2003/0069820 | A1 | 4/2003 | Hillmer et al. |
| 2003/0083903 | A1 | 5/2003 | Myers |
| 2003/0120588 | A1 | 6/2003 | Dodd et al. |
| 2003/0158755 | A1 | 8/2003 | Neuman |
| 2003/0229519 | A1 | 12/2003 | Eidex et al. |
| 2004/0064215 | A1 | 4/2004 | Greeven et al. |
| 2004/0093242 | A1 | 5/2004 | Cadigan et al. |
| 2004/0117205 | A1 | 6/2004 | Reardan et al. |
| 2004/0178112 | A1 | 9/2004 | Snyder |
| 2005/0209879 | A1 | 9/2005 | Chalmers |
| 2006/0062734 | A1 | 3/2006 | Melker et al. |
| 2006/0074717 | A1 | 4/2006 | Feldman et al. |
| 2008/0288281 | A1 | 11/2008 | Shell et al. |
| 2009/0144087 | A1 | 6/2009 | Kelsch et al. |
| 2009/0164376 | A1 | 6/2009 | Guthrie |
| 2009/0281824 | A1* | 11/2009 | Hardaway ......................... 705/2 |
| 2010/0312576 | A1* | 12/2010 | Brown et al. ..................... 705/2 |
| 2011/0173020 | A1* | 7/2011 | Bailey et al. ..................... 705/2 |
| 2012/0046970 | A1* | 2/2012 | Potts et al. ....................... 705/3 |

OTHER PUBLICATIONS

Non-Final Office Action for U.S. Appl. No. 12/411,075 mailed May 22, 2013.
Non-Final Office Action for U.S. Appl. No. 12/730,897 mailed Nov. 8, 2012.
Office Action for Canadian Application No. 2,485,034 dated Nov. 22, 2011.
Office Action for Canadian Application No. 2,485,031 dated Apr. 5, 2012.
Final Office Action for U.S. Appl. No. 12/820,750 mailed Jul. 6, 2012.
Non-Final Office Action for U.S. Appl. No. 12/480,907 mailed Sep. 12, 2012.
HealthWatch Technology—HWT Inc. Website obtained from Mar. 25, 2002 web.archive.org.
GAO publication GAO-01-662 "Medicaid: State Efforts to Control Improper Payments Vary" Jun. 2001.
Gregory J. Borca, "Technology Curtails Health Care Fraud" Managed Care Magazine, Apr. 2001.
McKesson & American Pharmacy Alliance Agree to Offer Omnlink Connectivity to Retail Pharmacies: More than 11,000 Pharmacies Gain Ability to Access Centralized Pharmacy Application. Bus. Wire. New York: Jul. 28, 1998 did=323992868&sid=4&Fmt=3 &clientId=19649&RQT&VNam=PQD>.
NDC Health Information Services Announces Contract with Arrow Pharmacy and Nutrition Centers for Pre & Post Editing Service. PR Newswire. New York: Mar. 11, 1999. p. 1. [Retr. Internet Oct. 30, 2007] URL: <http://proquest.umi.com/pqdweb?did=39644468 &sid=4&Fmt=3&clientId=19649&RQT=309&VNam=PQD>.
Titus, Nancy Riaden. Health Insurance Industry Battles High Cost Fraud, Journal Record, Nov. 20, 1993, pg no.
Sternberg et al., Using Cultural Algorithyms too Support Re-engineering of Rule-Based Expert systems in Dynamic Performance Environments: A Case Study in Fraud Detection, IEEE Transactions on Evolutionary Computation, vol. 1 No. 4, Nov. 1997, pp. 225-243.
Stefano, Bordoni. Insurance Faud Evaluation a Fuzzy Expert System, 2001 IEEE International Fuzzy Systems Conference, pp. 1491-1494.
Radcliffe, J.G.Y., "The Insurance Industry's Use of Databases to Prevent and Detect Fraud, and Improve Recoveries", European Convention on Security and Detection, Conference Publication No. 408, May 16-18, 1995, pp. 216-224.
NDC Health Provides United Drugs With Intelligent Valued-Added Network Services and New Information Solutions. PR Newswire. New York: Dec. 12, 2000. p. 1. [Retr. Internet Apr. 11, 2007] URL: <http://proquest.umi.com/pqdweb?did=65133864&sid=4&Fmt=3 &clientId=19649&RQT=309&VNam=PQD>.
Pharmacy Industry Leaders Launch Firm to Supply Real-Time Data. PR Newswire. New York: Jul. 30, 2001. p. 1. [Retr. Internet Oct. 30, 2007] URL: <http://proquest.umi.com/pqdweb?did=77135077 &sid=4&Fmt=11&clientId=19649&RQT=309&VNam=PQD>.
Wholesalers Get Into Technology Game. Chain Drug Review. Feb. 15, 1999. p. Rx20 [Retr. From Internet Oct. 30, 2007] URL:<http://www.accessmylibrary.com/coms/summary_0286-487914_ITM>.
Glaser, M. Computer Eliminates Third-Party Administrator. Drug Topics. Oradell: May 3, 1993. vol. 137, Issu.9; p. 54, 3 pgs. [Retr. From Internet Apr. 11, 2007]. URL: <http://proquest.umi.com/pqdweb?did=779533&sid=5&Fmt=11&clientId=19649 &RQT=309&VNam=PQD>.
International Search Report for PCT/US2003/051982 dated Jun. 2, 2004.
International Search Report for PCT/US2003/051992 dated Jun. 2, 2004.
Non-final Office Action for U.S. Appl. No. 10/439,423 mailed Jul. 31, 2008.
Final Office Action for U.S. Appl. No. 10/439,423 mailed Dec. 9, 2008.
Non-final Office Action for U.S. Appl. No. 11/961,559 mailed Mar. 3, 2010.
Non-final Office Action for U.S. Appl. No. 10/439,423 mailed Apr. 28, 2009.
Final Office Action for U.S. Appl. No. 10/439,423 mailed Dec. 24, 2009.
Final Office Action for U.S. Appl. No. 11/961,559 mailed Nov. 10, 2010.
Non-final Office Action for U.S. Appl. No. 12/411,043 mailed Feb. 8, 2011.
Advisory Action for U.S. Appl. No. 11/961,559 mailed Mar. 23, 2011.
Non-final Office Action for U.S. Appl. No. 12/411,075 mailed Jul. 7, 2011.
Final Office Action for U.S. Appl. No. 12/411,043 mailed Jul. 7, 2011.
Non-Final Office Action for U.S. Appl. No. 12/480,907 mailed Sep. 20, 2011.
Non-Final Office Action for U.S. Appl. No. 12/730,897 mailed Sep. 29, 2011.
Final Office Action for U.S. Appl. No. 12/411,075 mailed Oct. 26, 2011.
Non-Final Office Action for U.S. Appl. No. 12/820,750 mailed Feb. 1, 2012.
Final Office Action for U.S. Appl. No. 12/480,907 mailed May 4, 2012.
Final Office Action for U.S. Appl. No. 12/730,897 mailed Nov. 22, 2013.

\* cited by examiner

SYSTEMS AND METHODS FOR MONITORING CONTROLLED SUBSTANCE DISTRIBUTION

TECHNICAL FIELD

Aspects of the disclosure relate generally to healthcare transactions, and more particularly, to systems and methods for monitoring the distribution of controlled substances at healthcare providers.

BACKGROUND

The U.S. Drug Enforcement Agency is tasked with classifying certain prescription drugs under the Controlled Substances Act. Certain healthcare providers, such as pharmacies and hospitals can be licensed to distribute one or more of the classes of controlled substances to patients. While these healthcare providers are permitted to dispense certain classes of controlled substances, failure to properly dispense these controlled substances for a proper purpose can result in a healthcare provider's controlled substance license being revoked. Without a controlled substance license, most pharmacies and hospitals would not be able to operate effectively.

For small single-unit pharmacies and hospitals, the amount of prescription activity is not likely to be such that the owners or managers could not effectively monitor the level and frequency at which different classes of controlled substances are being prescribed. As such, when changes in prescription behavior or frequency occur, these owners or managers will likely be aware of the reasons for the change and can address it accordingly to make sure fraudulent activity is not occurring.

However, when the pharmacy or hospital is part of a chain or one of many owned by an ownership entity, it can be difficult or impossible for the ownership entity to fully monitor, in real-time, the controlled substance prescription trends for each individual pharmacy or hospital. Instead, the ownership entity must rely on the local management to properly monitor for potential fraud in the distribution of controlled substances. However, if the local management fails to properly monitor or is aware of and fails to correct any fraudulent activity related to the distribution of certain classes of controlled substances, the end result will likely be the pharmacy or hospital losing its controlled substance license and the chain or ownership entity closing the pharmacy or hospital.

The ability to monitor distribution trends for classes of controlled substances in real-time or near real-time at the healthcare provider level and comparing those trends to historical baselines for each distinct healthcare provider will allow an owner of a healthcare provider to quickly see when current trends related to prescribing controlled substances on the whole or at the class level exceed normal threshold levels and can immediately investigate the prescription habits of the particular healthcare provider to determine if any issues exist that may put its controlled substance license at risk.

BRIEF DESCRIPTION OF THE INVENTION

Exemplary embodiments of the invention may include systems and methods for monitoring the level of controlled substance distribution. In one embodiment, a computer-implemented method for monitoring the level of controlled substance distribution may be provided. A healthcare transaction for a patient may be received from a healthcare provider computer associated with a healthcare provider. Based at least in part on information included in the healthcare transaction, a determination of the class of controlled substance being prescribed to a patient as part of the healthcare transaction may be made. In addition, the current percentage of distribution by the healthcare provider for the class of controlled substance being prescribed may be determined. The current percentage of distribution may be compared to a predetermined threshold percentage of distribution for the call of controlled substance being prescribed in the healthcare transaction. A determination can be made as to whether the current percentage violates the predetermined threshold percentage of distribution for the call of controlled substance being prescribed. For example, the current percentage may violate the predetermined threshold percentage if the current percentage is greater than or greater than or equal to the predetermined threshold percentage. A notification can be transmitted to the healthcare provider based on a positive determination that the current percentage violates the predetermined threshold percentage.

In accordance with another embodiment, a system for monitoring the level of controlled substance distribution may be provided. The system may include at least one memory operable to store computer-executable instructions. The system may also include at least one processor configured to access the at least one memory and executing the computer-executable instructions. The at least one process may be configured to receive, from a healthcare provider computer associated with a healthcare provider, a healthcare transaction; determine, based at least in part on information included in the healthcare transaction, a class of controlled substance being prescribed to a patient; determine a current percentage of distribution by the healthcare provider for the class of controlled substance being prescribed; compare the current percentage of distribution to a predetermined threshold percentage of distribution for the class of controlled substance being prescribed; determine if the current percentage violates the predetermined threshold percentage of distribution for a class of controlled substance being prescribed; and direct the communication of a notification to the healthcare provider computer based on a positive determination that the current percentage violates the predetermined threshold percentage.

BRIEF DESCRIPTION OF THE DRAWINGS

Reference will now be made to the accompanying drawings, which are not necessarily drawn to scale, and wherein.

DETAILED DESCRIPTION OF EXEMPLARY EMBODIMENTS

Exemplary embodiments of the invention now will be described more fully hereinafter with reference to the accompanying drawings, in which exemplary embodiments of the invention are shown. This invention may, however, be embodied in many different forms and should not be construed as limited to the exemplary embodiments set forth herein; rather, these embodiments are provided so that this disclosure will be thorough and complete, and will fully convey the scope of the invention to those skilled in the art. Like numbers refer to like elements throughout.

Exemplary embodiments of the invention may include systems and methods for monitoring the distribution of controlled substances by healthcare providers as part of or in addition to the processing of a healthcare transaction. Healthcare transactions may be received and evaluated by a service provider prior to routing or otherwise communicating the healthcare transactions to various claims processors. The service provider's evaluation of the healthcare transaction may determine the healthcare provider submitting the transaction, if the healthcare provider is a member of the controlled substance monitoring network, any back office or corporation office associated with the healthcare provider, the drug or drugs being prescribed as part of the transaction, whether the drugs being prescribed as a part of the healthcare transaction belong to a class of controlled substances, and the number of pills or doses being prescribed of the drug. The service provider may then increment counters for the total scripts filled by the healthcare provider and the class of controlled substance being prescribed and may calculate a current percentage of the class of controlled substance being prescribed. The current percentage may be compared to a threshold percentage for the particular class of controlled substance for the particular healthcare provider to determine if the current percentage is greater than or greater than or equal to the threshold percentage (i.e. violates the threshold percentage). If the current percentage violates the threshold percentage, a notification can be automatically transmitted in real-time or near real-time to the corporate offices (i.e. the back office) of the healthcare provider so that a determination may be made if an investigation should be conducted of the current distribution levels of controlled substances for the healthcare provider.

System Overview

Figure 1:
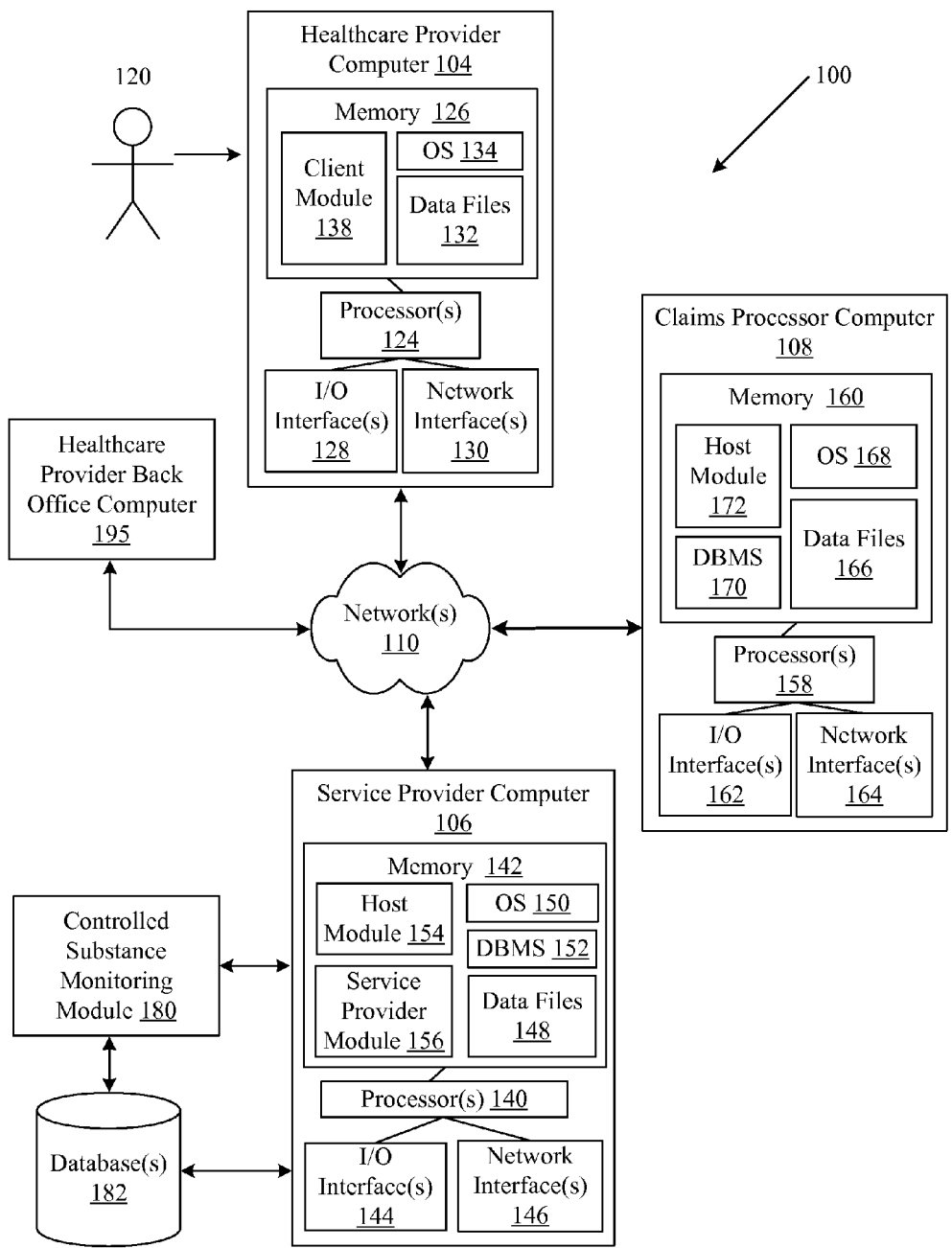
FIG. 1 illustrates an example overview of a system that facilitates the monitoring of the distribution of controlled substances by a healthcare provider as part of a processing of healthcare claims transactions, according to an example embodiment of the invention.

An example system 100 that facilitates the provision of monitoring of the distribution of controlled substances by a healthcare provider as part of a processing of healthcare claims transactions will now be described illustratively with respect to FIG. 1. As shown in FIG. 1, the system 100 may include at least one healthcare provider computer 104, at least one service provider computer 106, and at least one claims processor computer 108. As desired, each of the healthcare provider computer 104, service provider computer 106, and/or claims processor computer 108 may include one or more processing devices that may be configured for accessing and reading associated computer-readable media having stored thereon data and/or computer-executable instructions for implementing the various methods of the invention.

Additionally, in certain embodiments, the service provider computer 106 may include or otherwise be in communication with controlled substance monitoring module 180, or controlled substance monitoring application, which may access and/or be in communication with one or more suitable data storage devices, such as databases 182. The controlled substance monitoring module 180 may receive information associated with healthcare transactions, and may evaluate the types, number, percentage, and our amount of controlled substances to be distributed based at least in part on the information. Upon determining that a healthcare provider is distributing a controlled substance or a particular class of controlled substance at a rate that is greater than or greater than or equal to a predetermined trigger level, the controlled substance monitoring module 180 may trigger the generation of a notification message and direct the communication of the notification message to a healthcare provider back office computer 195 associated with the healthcare provider and/or a healthcare provider computer 104 from which the transaction originated. In certain exemplary embodiments, the healthcare provider back office computer 195 is located at or associated with a corporate office that owns, controls, or is affiliated with multiple healthcare providers, each having a healthcare provider computer 104 for submitting healthcare transactions. In one exemplary embodiment, the location of the healthcare provider back office computer 195 is the corporate offices of a pharmacy chain having multiple healthcare providers associated with the chain. According to an aspect of the invention, the notification message may include the name, number or some other unique identifier of the particular healthcare provider for which the notification is being sent, the class of controlled substance, the trigger level, and the current level of distribution of the class of controlled substance for the particular healthcare provider. The sending of the notification can alert the corporate level of the healthcare provider that an abnormal amount of controlled substances or particular classes of controlled substances are being distributed from one of its healthcare providers. The notification may alert the corporate level of the healthcare provider that an additional investigation into level of controlled substances or particular classes of controlled substances for the particular healthcare provider should be conducted.

Following the receipt of the notification, the corporation or management level of the healthcare provider or the healthcare provider itself may submit a request to modify the trigger levels for the controlled substances or one or more classes of the controlled substances from the healthcare provider back office computer 195 or the healthcare provider computer 104 to the service provider computer 106. The controlled substance monitoring module 180 may receive the request for modification of the trigger levels for a particular healthcare provider. The controlled substance monitoring module 180 may compare the modified trigger levels to the current trigger levels for the particular healthcare provider stored in the database(s) 182 and may update the database with the modified trigger levels in the database accordingly.

Generally, network devices and systems, including one or more of the healthcare provider computer 104, healthcare provider back office computer 195, service provider computer 106, and claims processor computer 108 may include or otherwise be associated with suitable hardware and/or software for transmitting and receiving data and/or computer-executable instructions over one or more communications links or networks. These network devices and systems may also include any number of processors for processing data and executing computer-executable instructions, as well as other internal and peripheral components that are well known in the art. Further, these network devices and systems may include or be in communication with any number of suitable memory devices operable to store data and/or computer-executable instructions. By executing computer-executable instructions, each of the network devices may form a special purpose computer or particular machine. As used herein, the term "computer-readable medium" describes any form of suitable memory or memory device.

As shown in FIG. 1, the healthcare provider computer 104, healthcare provider back office computer 195, service provider computer 106, and claims processor computer 108 may be in communication with each other via one or more networks, such as network 110, which as described below can include one or more separate or shared private and public networks, including the Internet or a publicly switched telephone network. Each of these components—the healthcare provider computer 104, healthcare provider back office computer 195, service provider computer 106, and claims processor computer 108, and the network 110—will now be discussed in further detail.

The healthcare provider computer 104 may be associated with a healthcare provider, such as, for example, a pharmacy, physician's office, hospital, etc. In certain embodiments, the healthcare provider may be associated with a group of healthcare providers, such as a pharmacy chain. The healthcare provider computer 104 may be any suitable processor-driven device that facilitates the processing of healthcare requests made by patients or consumers and the communication of information associated with healthcare transactions to the service provider computer 106, such as a server computer, a mainframe computer, one or more networked computers, a desktop computer, a personal computer, a digital assistant, a personal digital assistant, a digital tablet, an Internet appliance, an application-specific circuit, microcontroller, minicomputer, or any other processor-based device. In certain embodiments, the healthcare provider computer 104 may be a suitable point of sale device associated with a healthcare provider. The execution of the computer-implemented instructions by the healthcare provider computer 104 may form a special purpose computer or other particular machine that is operable to facilitate the processing of healthcare requests made by patients and the communication of information associated with healthcare transactions to a service provider computer 106. Additionally, in certain embodiments of the invention, the operations and/or control of the healthcare provider computer 104 may be distributed amongst several processing components.

In addition to having one or more processors 124, the healthcare provider computer 104 may include one or more memory devices 126, one or more input/output ("I/O") interface(s) 128, and one or more network interface(s) 130. The memory devices 126 may be any suitable memory devices, for example, caches, read only memory devices, random access memory devices, magnetic storage devices, removable storage devices, etc. The memory devices 126 may store data, executable instructions, and/or various program modules utilized by the healthcare provider computer 104, for example, data files 132, an operating system ("OS") 134, and/or a client module 138. The data files 132 may include any suitable data that facilitates the receipt and/or processing of healthcare requests by the healthcare provider computer 104 and the generation and/or processing of healthcare transactions that are communicated to the service provider computer 106. For example, the data files 132 may include, but are not limited to, healthcare information and/or contact information associated with one or more patients, information associated with the service provider computer 106, information associated with one or more claims processors, and/or information associated with one or more healthcare transactions. The OS 134 may be a suitable software module that controls the general operation of the healthcare provider computer 104. The OS 134 may also facilitate the execution of other software modules by the one or more processors 124, for example, the client module 138. The OS 134 may be, but is not limited to, Microsoft Windows®, Apple OSX™, Linux, Unix, or a mainframe operating system. The client module 138 may be an Internet browser or other suitable software, including a dedicated program, for interacting with the service provider computer 106. For example, a user 120 such as a pharmacist or other pharmacy employee may utilize the client module 138 in preparing and providing a prescription claim request to the service provider computer 106 for delivery to the appropriate claims processor computer 108 or other third-party for adjudication or other coverage/benefits determination. The healthcare provider computer 104 may also utilize the client module 138 to retrieve or otherwise receive data, messages, or responses from the service provider computer 106 and/or other components of the system 100. For example, in certain embodiments, the client module 138 may be utilized to receive notification messages when predetermined trigger levels for controlled substances or particular classes of controlled substances are met or exceeded from the service provider computer 106 as will be described.

In operation, the healthcare provider computer 104 may receive information associated with a healthcare request for a patient. As one example, the healthcare provider computer 104 may receive a healthcare request for a patient at a point of sale, such as in a pharmacy during a prescription fulfillment or at a physician's office during the provision of a healthcare service. As another example, the healthcare provider computer 104 may electronically receive a healthcare request from a patient computer, phone, or other patient device. The healthcare provider computer 104 may generate a healthcare transaction for the request and information associated with the healthcare transaction may be communicated to the service provider computer 106. The healthcare provider computer 104 may then receive one or more responses to the healthcare transaction, such as an adjudicated reply, a rejection message, a notification message when predetermined trigger levels for controlled substances or particular classes of controlled substances are met or exceeded, etc.

The one or more I/O interfaces 128 may facilitate communication between the healthcare provider computer 104 and one or more input/output devices, for example, one or more user interface devices, such as, a display, keypad, control panel, touch screen display, remote control, microphone, etc. that facilitate user interaction with the healthcare provider computer 104. For example, the one or more I/O interfaces 128 may facilitate entry of information associated with a healthcare transaction or healthcare claim request by an employee 120 of a healthcare provider, such as a pharmacy employee. The one or more network interfaces 130 may facilitate connection of the healthcare provider computer 104 to one or more suitable networks, for example, the network 110 illustrated in FIG. 1. In this regard, the healthcare provider computer 104 may receive and/or communicate information to other network components of the system 100, such as the service provider computer 106.

With continued reference to FIG. 1, the service provider computer 106 may include, but is not limited to, any suitable processor-driven device that is configured for receiving, processing, and fulfilling requests from the healthcare provider computer 104 and/or claims processor computer 108 relating to prescription, pharmacy, benefits, and/or healthcare transactions and/or other activities. In certain embodiments, the service provider computer 106 may be a switch/router that routes healthcare transactions and/or other healthcare requests. For example, the service provider computer 106 may route billing requests and/or prescription claim requests communicated from the healthcare provider computer 104 to a claims processor computer 108, such as a pharmacy benefits manager (PBM), an insurer, a Medicare payor, or other third-party payor. In certain embodiments, the service provider computer 106 may include a suitable host server, host module, or other software that facilitates the receipt of a healthcare transaction from a healthcare provider computer 104 and/or the routing of the received healthcare transaction to a claims processor computer 108. Any number of healthcare provider computers 104, healthcare provider back office computers 195, and/or claims processor computers 108 may be in communication with the service provider computer 106 as desired in various embodiments of the invention.

The service provider computer 106 may include any number of special purpose computers or other particular machines, application-specific circuits, microcontrollers, personal computers, minicomputers, mainframe computers, servers, networked computers, and/or other processor-driven devices. In certain embodiments, the operations of the service provider computer 106 may be controlled by computer-executed or computer-implemented instructions that are executed by one or more processors associated with the service provider computer 106 to form a special purpose computer or other particular machine that is operable to facilitate the receipt, routing, and/or processing of healthcare transactions. The one or more processors that control the operations of the service provider computer 106 may be incorporated into the service provider computer 106 and/or in communication with the service provider computer 106 via one or more suitable networks. In certain exemplary embodiments, the operations and/or control of the service provider computer 106 may be distributed amongst several processing components.

Similar to the healthcare provider computer 104, the service provider computer 106 may include one or more processors 140, one or more memory devices 142, one or more input/output ("I/O") interface(s) 144, and one or more network interface(s) 146. The one or more memory devices 142 may be any suitable memory devices, for example, caches, read only memory devices, random access memory devices, magnetic storage devices, removable memory devices, etc. The one or more memory devices 142 may store data, executable instructions, and/or various program modules utilized by the service provider 106, for example, data files 148, an operating system ("OS") 150, the host module 154, a service provider module 156, and a database management system ("DBMS") 152 to facilitate management of data files 148 and other data stored in the memory devices 142 and/or one or more databases 182. The OS 150 may be, but is not limited to, Microsoft Windows®, Apple OSX™, Linux, Unix, or a mainframe operating system. The OS 150 may be a suitable software module that controls the general operation of the service provider computer 106 and/or that facilitates the execution of other software modules.

The service provider module 156 may be operable to perform one or more pre-edits on a received healthcare transaction prior to routing or otherwise communicating the received healthcare transaction to a suitable claims processor computer 108. Additionally, the service provider module 156 may be operable to perform one or more post-edits on an adjudicated reply or response that is received from a claims processor computer 108 for a healthcare transaction prior to routing the adjudicated reply to the healthcare provider computer 104. A wide variety of different pre-edits and/or post-edits may be performed as desired in various embodiments of the invention.

In certain embodiments, a controlled substance monitoring module 180 may be incorporated into the service provider module 156 and/or in communication with the service provider module 156, which may determine if the healthcare provider associated with a received healthcare transaction has violated a threshold percentage associated with the healthcare provider for a class of controlled substances.

According to one exemplary embodiment, the data files 148 may store healthcare transaction records associated with communications received from various healthcare provider computers 104, healthcare provider back office computers 195, and/or various claims processor computers 108. The data files 148 may also store any number of suitable routing tables that facilitate determining the destination of communications received from a healthcare provider computer 104, healthcare provider back office computer 195, or claims processor computer 108. The host module 154 may receive, process, and respond to requests from the client module 138 of the healthcare provider computer 104, receive, process and respond to requests from the healthcare provider back office computer 195, and may further receive, process, and respond to requests of the host module 172 of the claims processor computer 108. The service provider computer 106 may include additional program modules for performing other processing methods described herein. Those of ordinary skill in the art will appreciate that the service provider computer 106 may include alternate and/or additional components, hardware or software without departing from exemplary embodiments of the invention.

A controlled substance monitoring module 180 or controlled substance monitoring application may also be operative with the service provider computer 106. The controlled substance monitoring module 180 may include computer-executable instructions for processing healthcare transactions in order to detect the particular healthcare service provider, whether a controlled substance is being prescribed, the class of the controlled substance being prescribed, the amount of pills or other units of prescription that have been prescribed, and/or if the prescription has been approved by a claims processor based at least in part on the healthcare transaction. In one exemplary embodiment, a service provider computer 106 may receive and process a healthcare transaction received from a healthcare provider computer 104 to determine whether controlled substances are being prescribed as a part of the healthcare transaction. If so, the service provider computer 106 may transmit all or a portion of the healthcare transaction, for example the prescription claim request, to the controlled substance monitoring module 180 to conduct its analysis, which may be based on any number of trigger levels, factors, parameters, and/or information included in healthcare provider history files stored in one or more databases 182 accessed by the controlled substance monitoring module 180.

According to one embodiment, as described in more detail herein, the service provider computer 106 may receive a healthcare transaction from a healthcare provider, such as, a prescription claim request for a prescription fill or refill. Upon receipt of the healthcare transaction, the controlled substance monitoring module 180 can analyze healthcare provider identifying information included within the healthcare transaction to determine whether the healthcare provider is receiving controlled substance level monitoring services. For instance, the service provider may determine whether the healthcare provider identifying information, such as, a National Provider Identifier (NPI), contained within or identified in the healthcare transaction matches one or more NPI numbers stored in one or more databases 182 identifying healthcare providers receiving controlled substance lever monitoring services.

Similarly, preferences, rules, and/or other parameters associated with a healthcare provider or group of healthcare providers may be received in a healthcare transaction or pre-stored in one or more databases 182 for access by the controlled substance monitoring module 180. In this regard, the controlled substance monitoring module 180 may identify one or more trigger levels or parameters that are applicable with regard to the healthcare provider and the particular healthcare transaction. For example, the controlled substance monitoring module 180 may identify one or more trigger levels or parameters based upon an identity of the healthcare provider that submitted the claim transaction or a group of healthcare providers (e.g. a pharmacy chain) in which the healthcare provider is included. In addition, or in the alternative, the trigger level(s) identified may include trigger levels associated with various United States Drug Enforcement Agency classes or schedules (collectively referred to herein as classes) of controlled substances and/or other parameters that are utilized to evaluate the amount of controlled substances or particular classes of controlled substances that have been prescribed by a service provider over a predetermined amount of time. The evaluation is used to determine whether the service provider has met or exceeded a predetermined trigger level for distribution of controlled substances or a class of controlled substance over the predetermined amount of time. In addition, the evaluation is used to determine if a notification should be sent to the healthcare provider or the corporate or management level of the healthcare provider or group of healthcare providers (e.g. a pharmacy chain). In addition to or as an alternative to utilizing certain trigger levels associated with a healthcare provider or group of healthcare providers, one or more default trigger levels derived independent of the historical script filling information of the healthcare provider or group of healthcare providers (e.g. pharmacy chain) may be accessed (from for example the database 182) and utilized by the controlled substance monitoring module 180.

If the service provider computer 106 determines that the healthcare transaction is not being submitted by a healthcare provider for which controlled substance monitoring services are being provided, then the healthcare transaction may be routed or otherwise communicated to a suitable claims processor computer 108 or designated payor.

Additionally, the controlled substance monitoring module 180 may store or direct the storage of information associated with the healthcare transaction in, for example, the data storage devices 182. For instance, the controlled substance monitoring module 180 may determine and/or direct the storage of information that associates healthcare providers with a healthcare provider back office computer 195. Additionally, the controlled substance monitoring module 180 may determine that a healthcare transaction includes a prescription, a prescription for a controlled substance and/or the class of the controlled substance and can update or increment counters associated with each and associated with the healthcare provider in the database(s) 182. In addition or in the alternative, the controlled substance monitoring module 180 can determine the number of pills or other unit of dosage and increment counters associated with each and associated with the healthcare provider in the database(s) 182.

The controlled substance monitoring module 180 may determine whether the claim transaction has been paid or approved for payment prior to incrementing counters and evaluating current counts against trigger levels. For example, the service provider computer 106 may route the claim to the claims processor computer 108 for adjudication and receive an adjudicated reply or response from the claims processor computer 108. At least a portion of the adjudicated reply may be passed to the controlled substance monitoring module 180, and the controlled substance monitoring module 180 may analyze the received information associated with the adjudicated reply in order to determine whether the claim has been paid or approved for payment. If the claim has been paid or approved, then the controlled substance monitoring module 180 may increment the particular counters for total prescriptions and for controlled substances or a particular class of controlled substance, evaluate if any trigger levels have been met or exceeded and, as necessary, send any notification of trigger levels being met or exceeded to the healthcare provider back office computer 195 or healthcare provider computer 104.

In certain embodiments, the controlled substance monitoring module 180 may store or direct the storage of information associated with the healthcare transaction in, for example, the data storage device 182. For instance, the controlled substance monitoring module 180 may update counters associated with each healthcare provider including, but not limited to, total scripts prescribed by the healthcare provider, total scripts of class 2 controlled substances prescribed by the healthcare provider, total scripts of class 3 controlled substances prescribed by the healthcare provider, total scripts of class 4 controlled substances prescribed by the healthcare provider; total scripts of class 5 controlled substances prescribed by the healthcare provider, predetermined threshold percentages for classes 2-5 of controlled substances for the healthcare provider; updated threshold percentages for any of the class 2-5 controlled substances as provided or requested by the healthcare provider or healthcare provider back office, and any notifications sent to a healthcare provider or healthcare provider back office.

In certain exemplary embodiments, the notification of trigger levels being met or exceeded may be communicated directly to the healthcare provider (e.g. a healthcare provider back office computer 195, a healthcare provider computer 104, or any other system or device associated with the healthcare provider, such as a printer, fax machine, handheld device, or other computing device) by the controlled substance monitoring module 180 via one or more suitable networks 110. In other embodiments, the controlled substance monitoring module 180 may direct the communication of the notification of trigger levels being met or exceeded through one or more other components of the system 100, such as the service provider computer 106. For example, the notification of trigger levels being met or exceeded may be routed or otherwise communicated to the healthcare provider back office computer 195 or the healthcare provider computer 104 by the service provider computer 106.

The database(s) 182 may be operable to store information associated with various trigger levels, healthcare provider groupings or associations, rules, parameters, and/or edits that may be utilized by the controlled substance monitoring module 180 to extract the necessary information from the healthcare transactions and/or to conduct an evaluation of the level or number of controlled substances being prescribed or provided by a healthcare provider. For example, rules or parameters may be received from one or more other components of the system 100, such as the healthcare provider computer 104 and at least a portion of the received rules may be stored. Additionally, the database(s) 182 may be operable to store information associated with healthcare providers enrolled in or receiving controlled substance level monitoring, such as an identifier for the healthcare provider (e.g. the NPI), a chain or association that the healthcare provider is a member of (for determining the healthcare provider back office computer 195 associated with the healthcare provider) or alternatively an identification of the healthcare provider back office computer 195 associated with the healthcare provider, a historical database of the total number of prescriptions filled by the healthcare provider (which can be parsed over a predetermined amount of time (e.g. a year or more, a calendar quarter, a month, two months, bi-monthly, weekly, and/or daily) and a historical database of the total number and class of controlled substances prescriptions filled by the healthcare provider (which can be parsed over a predetermined amount of time (e.g. a year or more, a calendar quarter, a month, two months, bi-monthly, weekly, and/or daily), and the like, any of which may be accessed, updated, or otherwise used by the controlled substance monitoring module 180 when processing healthcare transactions. In certain embodiments, the database (s) 182 may additionally store billing information associated with the healthcare transactions and/or reports associated with the healthcare transactions and/or processing of the healthcare transactions. The database(s) 182 may be accessible by the controlled substance monitoring module 180 and/or the service provider computer 106.

The operations of the controlled substance monitoring module 180 and/or the data storage devices 182 are described in greater detail below with reference to FIGS. 3-4B.

With continued reference to the service provider computer 106, the one or more I/O interfaces 144 may facilitate communication between the service provider computer 106 and one or more input/output devices, for example, one or more user interface devices, such as a display, keypad, control panel, touch screen display, remote control, microphone, etc. that facilitate user interaction with the service provider computer 106. The one or more network interfaces 146 may facilitate connection of the service provider computer 106 to one or more suitable networks, for example, the network 110 illustrated in FIG. 1. In this regard, the service provider computer 106 may communicate with other components of the system 100.

With continued reference to FIG. 1, the claims processor computer 108 may be any suitable processor-driven device that facilitates receiving, processing, and/or fulfilling healthcare transactions and/or healthcare transactions received from the service provider computer 106. For example, the claims processor computer 108 may be a processor-driven device associated with a pharmacy benefits manager (PBM), an insurer, a government payor, or a claims clearinghouse. As desired, the claims processor computer 108 may include any number of special purpose computers or other particular machines, application-specific circuits, microcontrollers, personal computers, minicomputers, mainframe computers, servers, and the like. In certain embodiments, the operations of the claims processor computer 108 may be controlled by computer-executed or computer-implemented instructions that are executed by one or more processors associated with the claims processor computer 108 to form a special purpose computer or other particular machine that is operable to facilitate the receipt, processing, and/or fulfillment of healthcare transaction requests received from the service provider computer 106. The one or more processors that control the operations of the claims processor computer 108 may be incorporated into the claims processor computer 108 and/or in communication with the claims processor computer 108 via one or more suitable networks. In certain embodiments of the invention, the operations and/or control of the claims processor computer 108 may be distributed amongst several processing components.

Similar to other components of the system 100, the claims processor computer 108 may include one or more processors 158, one or more memory devices 160, one or more input/output ("I/O") interface(s) 162, and one or more network interfaces 164. The one or more memory devices 160 may be any suitable memory devices, for example, caches, read only memory devices, random access memory devices, magnetic storage devices, removable memory devices. The one or more memory devices 160 may store data, executable instructions, and/or various program modules utilized by the claims processor computer 108, for example, data files 166, an operating system ("OS") 168, a database management system ("DBMS") 170, and a host module 172. The data files 166 may include any suitable information that is utilized by the claims processor computer 108 to process healthcare transactions, for example, patient profiles, patient insurance information, other information associated with a patient, information associated with a healthcare provider, etc. The operating system (OS) 168 may be a suitable software module that controls the general operation of the claims processor computer 108. The OS 168 may also facilitate the execution of other software modules by the one or more processors 158, for example, the DBMS 170 and/or the host module 172. The OS 168 may be, but is not limited to, Microsoft Windows®, Apple OSX™, Linux, Unix, or a mainframe operating system. The DBMS 170 may be a suitable software module that facilitates access and management of one or more databases that are utilized to store information that is utilized by the claims processor computer 108 in various embodiments of the invention. The host module 172 may initiate, receive, process, and/or respond to requests, such as healthcare transactions or claim requests, from the host module 154 of the service provider 106. The claims processor computer 108 may include additional program modules for performing other pre-processing or post-processing methods described herein. Those of ordinary skill in the art will appreciate that the claims processor 108 computer may include alternate and/or additional components, hardware or software without departing from example embodiments of the invention.

The one or more I/O interfaces 162 may facilitate communication between the claims processor computer 108 and one or more input/output devices, for example, one or more user interface devices, such as a display, keypad, control panel, touch screen display, remote control, microphone, etc. that facilitate user interaction with the claims processor computer 108. The one or more network interfaces 164 may facilitate connection of the claims processor computer 108 to one or more suitable networks, for example, the network 110 illustrated in FIG. 1. In this regard, the claims processor computer 108 may receive healthcare transactions and/or other communications from the service provider computer 106, and the claims processor computer 108 may communicate information associated with processing claim transactions to the service provider.

With continued reference to FIG. 1, the healthcare provider back office computer 195 may be one or more computers associated with a group of healthcare providers, such as a chain of pharmacies. The healthcare provider back office computer 195 may include components that are similar to those of other devices included in the system 100 such as the healthcare provider computer 104. For example, the healthcare provider back office computer 195 may be a processor-driven device that is operable or configured to receive, from the service provider computer 106 and/or the controlled substance monitoring module 180 notification messages when predetermined trigger levels for controlled substances or particular classes of controlled substances are met or exceeded. Additionally, the healthcare provider back office computer 195 may be operable or configured to provide updated trigger levels for controlled substances or particular classes of controlled substances for one or more healthcare providers.

The network 110 may include any telecommunication and/or data network, whether public, private, or a combination thereof, including a local area network, a wide area network, an intranet, the Internet, intermediate hand-held data transfer devices, and/or any combination thereof and may be wired and/or wireless. The network 110 may also allow for real-time, off-line, and/or batch transactions to be transmitted between or among the healthcare provider computer 104, the service provider computer 106 (including the controlled substance monitoring module), the healthcare provider back office computer 195, and the claims processor computer 108. Due to network connectivity, various methodologies, as described herein may be practiced in the context of distributed computing environments. Although the service provider computer 106 is shown for simplicity as being in communication with the healthcare provider computer 104 or the claims processor computer 108 via one intervening network 110, it is to be understood that any other network configuration is possible. For example, intervening network 110 may include a plurality of networks, each with devices such as gateways and routers for providing connectivity between or among networks 110. Instead of or in addition to a network 110, dedicated communication links may be used to connect the various devices in accordance with an example embodiment of the invention. For example, the service provider computer may form the basis of network 110 that interconnects the healthcare provider computer 104, the healthcare provider back office computer 195, and the claims processor computer 108.

Those of ordinary skill in the art will appreciate that the system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one embodiment, the service provider computer 106 (or other computer) may be implemented as a specialized processing machine that includes hardware and/or software for performing the methods described herein. In addition, at least a portion of the processor and/or processing capabilities of the service provider computer 106 and/or the controlled substance monitoring module 180, may be implemented as part of the claims processor computer 108. Accordingly, embodiments of the invention should not be construed as being limited to any particular operating environment, system architecture, or device configuration.

Operational Overview

Figure 2:
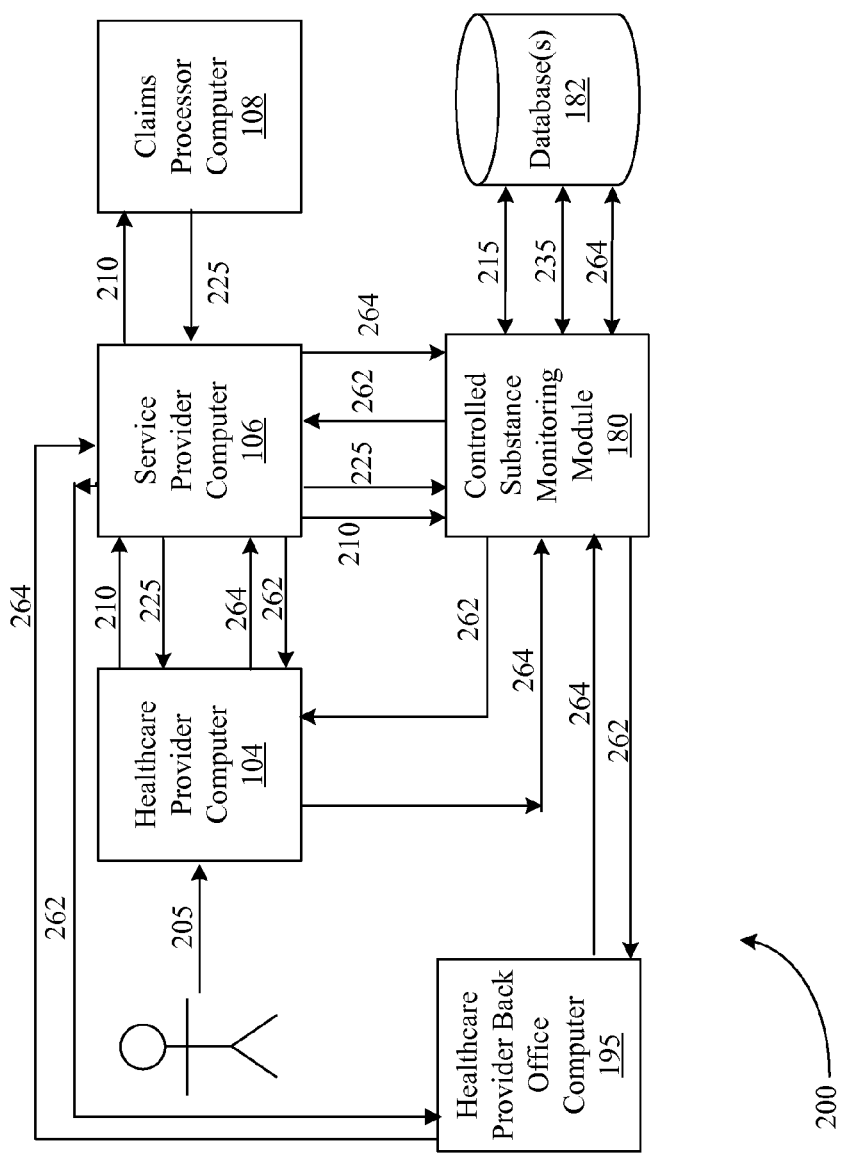
FIG. 2 is a diagram of example data flow for monitoring of the distribution of controlled substances by a healthcare provider as part of a processing of healthcare claims transactions that are processed through a service provider, according to illustrative embodiments of the invention.

FIG. 2 is a diagram of one example data flow 200 for evaluating healthcare transactions that are processed through a service provider, such as the service provider computer 106 illustrated in FIG. 1, in order to determine if controlled substance monitoring should be conducted and conducting that controlled substance monitoring. With reference to FIG. 2, a healthcare provider computer 104 illustrated in FIG. 1, may receive a healthcare request 205 from a patient, such as a healthcare request 205 for a prescription drug, non-prescription drug, other product, or service. The healthcare request 205 may be received in-person or electronically as desired in various embodiments of the invention. For example, a patient may request a medication product at a pharmacy or physician's offices. As another example, a patient may communicate a healthcare request 205 to a healthcare provider computer 104 via one or more suitable network connections. For example, a purchase request for a product may be communicated to a healthcare provider computer 104 from a customer computer via a web portal hosted by the healthcare provider computer 104.

The healthcare provider computer 104 may receive and process the request 205 to generate a healthcare transaction 210, such as a healthcare claim request or a prescription claim request, and the healthcare transaction 210 may be communicated by the healthcare provider computer 104 to the service provider computer 106. According to an example embodiment of the invention, the healthcare transaction 210 may be in accordance with a version of a National Council for Prescription Drug Programs (NCPDP) Telecommunication Standard, although other standards may be utilized as well. As desired, the healthcare transaction 210 may include a Banking Identification Number (BIN) and/or a Processor Control Number (PCN) for identifying a particular claims processor computer or payer, such as the claims processor computer 108 illustrated in FIG. 1, as a destination for the healthcare transaction 210. In addition, the healthcare transaction 210 may also include information relating to the patient, payor, prescriber, healthcare provider, and/or the prescribed or administered drug, product, or service. As an example, the healthcare transaction 210 received by the service provider computer 106 may include one or more of the following information:

Payor ID/Routing Information
BIN Number (i.e. Banking Identification Number) and/or Processor Control Number (PCN) that designates a destination of the healthcare transaction 210
Patient Information
Name (e.g. Patient Last Name, Patient First Name, etc.)
Date of Birth of Patient
Age of Patient
Gender
Patient Address (e.g. Street Address, Zip Code, etc.)
Patient Contact Information (e.g. Patient Telephone Number, email address, etc.)
Patient Health Condition Information
Patient ID or other identifier
Insurance/Coverage Information
Cardholder Name (e.g. Cardholder First Name, Cardholder Last Name)
Cardholder ID and/or other identifier (e.g. person code)
Group ID and/or Group Information
State Payor Information
Prescriber Information
Primary Care Provider ID or other identifier (e.g. NPI code)
Primary Care Provider Name (e.g. Last Name, First Name)
Prescriber ID or other identifier (e.g. NPI code, DEA number)
Prescriber Name (e.g. Last Name, First Name)
Prescriber Contact Information (e.g. Telephone Number)
Pharmacy or other Healthcare Provider Information (e.g. store name, chain identifier, etc.)
Pharmacy or other Healthcare Provider ID (e.g. NPI code)
Claim Information
Drug or product information (e.g. National Drug Code (NDC))
Prescription/Service Reference Number
Date Prescription Written
Quantity Dispensed
Number of Days Supply
Diagnosis/Condition
Pricing information for the drug or product (e.g. network price, Usual & Customary price)
One or more NCPDP Message Fields One or more Drug Utilization (DUR) Codes Date of Service.

With continued reference to FIG. 2, the service provider computer 106 may receive the healthcare transaction 210 from the healthcare provider computer 104, and the service provider computer 106 may process the healthcare transaction 210. As desired, the service provider computer 106 may perform one or more pre-edits on the healthcare transaction 210. The pre-edits may verify, add, and/or edit information included in the healthcare transaction 210 prior to the healthcare transaction 210 being communicated to an appropriate claims processor computer 108. In certain embodiments, a determination may be made as to whether the healthcare transaction 210 is from a healthcare provider that is receiving controlled substance level monitoring based at least in part on information contained in the healthcare transaction.

According to an example embodiment, the service provider computer 106 may utilize at least a portion of the information included in the healthcare transaction 210, such as a BIN/PCN, to determine the appropriate claims processor computer 108 to route the healthcare transaction 210 to. The service provider computer 106 may also include a routing table, perhaps stored in memory, for determining which claims processor computer 108 to route the healthcare transaction 210 to. The healthcare transaction 210 and/or a copy thereof may be routed or otherwise communicated by the service provider computer 106 to an appropriate claims processor computer 108 associated with a designated payor for adjudication.

The claims processor computer 108 may receive and adjudicate or otherwise process the healthcare transaction 210. For example, the claims processor computer 108 may determine benefits coverage for the healthcare transaction 210 according to an adjudication process associated with eligibility, pricing, and/or utilization review. The claims processor computer 108 may transmit an adjudicated reply 225 or response for the healthcare transaction 210 to the service provider computer 106. The service provider computer 106 may receive the adjudicated reply 225 from the claims processor computer 108. As desired, the service provider computer 106 may perform any number of post-edits on the adjudicated reply 225. The adjudicated reply 225 may then be routed or otherwise communicated by the service provider computer 106 to the healthcare provider computer 104.

If the healthcare provider is receiving or is signed up to receive controlled substance level monitoring, the healthcare transaction 210, a copy of the transaction 210, and/or information included in the transaction 210 may be communicated to a suitable controlled substance monitoring module, such as the controlled substance monitoring module 180 shown in FIG. 1, for processing. In addition, the adjudicated reply 225 or a copy of the adjudicated reply 225 may be routed or otherwise communicated to the controlled substance monitoring module 180. The controlled substance monitoring module 180 may receive the healthcare transaction 210 and the controlled substance monitoring module 180 may evaluate the controlled substance distribution levels for the healthcare provider. In doing so, the controlled substance monitoring module 180 may access information 215 associated with one or more threshold percentage levels for controlled substances generally or for each class of controlled substance to determine if the threshold percentage levels have been violated. The controlled service monitoring module may also access information 235 associated with the healthcare provider (e.g. a pharmacy chain). A wide variety of information may be accessed as desired in various embodiments, including but not limited to, NPI and other identifiers for the healthcare provider, association information between healthcare providers (i.e. information associating an entire chain or pharmacies together) and identification as to where to transmit notifications of violations of a threshold parameter, such as notification of an email address or network address associated with the healthcare provider back office computer 195).

If a controlled substance is being prescribed as part of the healthcare transaction and the controlled substance monitoring module 180 determines that the current level of percentage of the particular class of controlled substance being prescribed is greater than or greater than or equal to a predetermined threshold for the particular class of controlled substance, the controlled substance monitoring module 180 may generate one or more suitable notifications, reports or messages 262 indicating a threshold percentage for the particular class of controlled substance has been violated (i.e. exceeded and/or equaled). The notification, report, or message 262 may be communicated from the controlled substance monitoring module 180 to the healthcare provider back office computer 195 and/or the healthcare provider computer 104.

Once a notification that a threshold percentage has been violated has been received by the healthcare provider back office computer 195 or healthcare provider computer 104, the healthcare provider may be made aware of violation of the threshold percentage and conduct an evaluation or investigation of the particular healthcare provider to determine why the violation occurred. The healthcare provider back office computer 195 or healthcare provider computer 104 may then transmit information 264 to the service provider computer 106 of the controlled substance monitoring module 180 requesting that one or more threshold percentages be adjusted or updated in the database.

As described herein, healthcare transactions may be examined as they are routed to or through a service provider computer 106. In this regard, an evaluation of the level of controlled substances being distributed by a healthcare provider and notifications if the level meets or exceeds predetermined trigger levels can be provided in real-time or near real-time as the healthcare transactions are routed to or through the service provider computer 106. FIG. 3 is a flow chart of an example method 300 for determining as initial baseline for trigger levels for different classes of controlled substances for a healthcare provider for use in monitoring the distribution levels of controlled substances of the healthcare provider in accordance with one exemplary embodiment. The exemplary method 300 may be performed by a suitable service provider computer 106 and/or a controlled substance monitoring module 180. The controlled substance monitoring module 180 may be associated with the service provider computer 106, such as the service provider computer 106 and the controlled substance monitoring module 180 illustrated in FIG. 1. Alternatively, the controlled substance monitoring module may be associated with a third-party computer.

Figure 3:
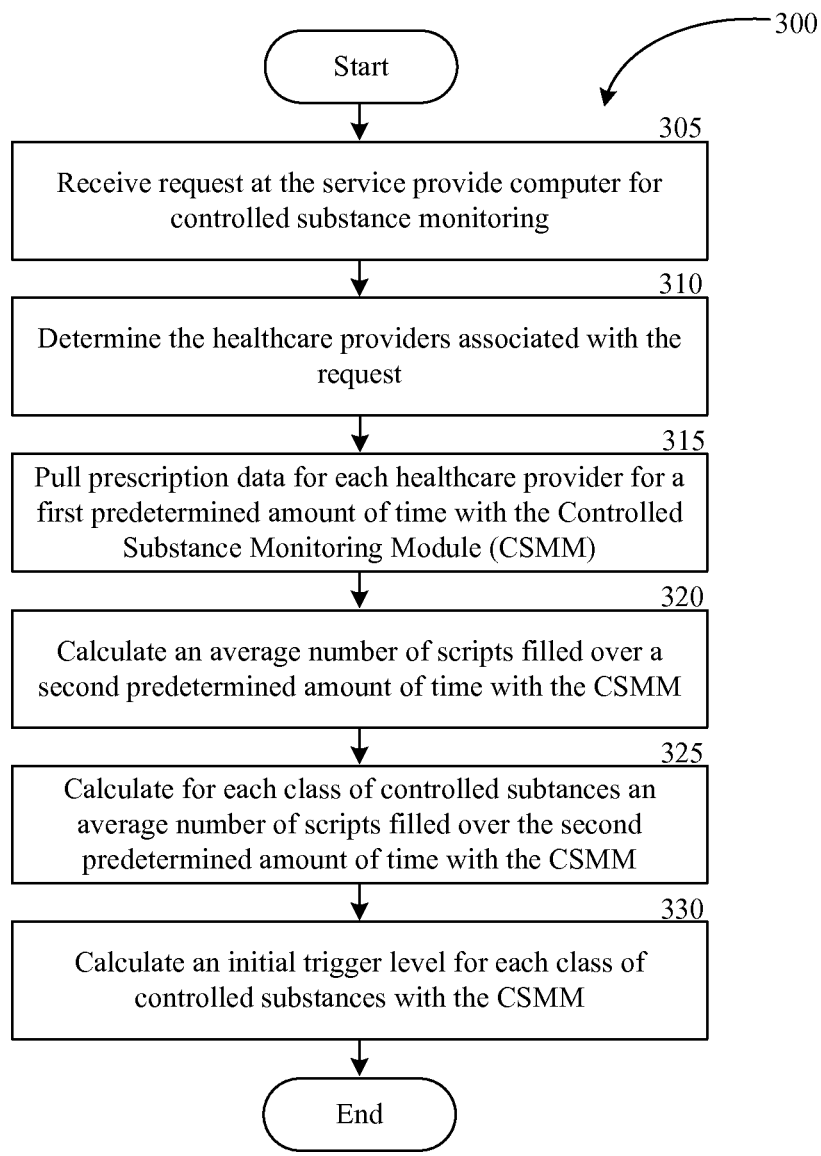
FIG. 3 is a flow chart of an example method for determining an initial baseline for trigger levels for different classes of controlled substances for a healthcare provider in order to monitor the distribution levels of controlled substances of the healthcare provider, according to an illustrative embodiment of the invention.

Referring now to FIGS. 1 and 3, the exemplary method 300 begins at the START step and proceeds to step 305, where a request is received for controlled substance level monitoring. In certain exemplary embodiments, the request may be sent by the healthcare provider computer 104 or the healthcare provider back office computer 195 and received by the service provider at the service provider computer 106. In addition or alternatively, a request may be made by a healthcare provider or the corporate offices of a pharmacy chain having multiple healthcare providers associated with the chain by phone, email, letter, facsimile or any other known method of correspondence requesting to receive controlled substance level monitoring. In step 310, the healthcare providers associated with the request are determined. In certain exemplary embodiments, the determination is made by the service provider computer 106. For example, the service provider computer 106 may parse the request to determine the healthcare providers associated with the request. Alternatively, the service provider computer 106 may query the database 182 to determine the healthcare providers associated with the request.

Historical prescription data for a first predetermined amount of time is pulled for each healthcare provider associated with the request in step 315. In certain exemplary embodiments, the data is pulled by the controlled substance monitoring module 180 from the database 182. The first predetermined amount of time is one year in certain exemplary embodiments. Alternatively, the first predetermined amount of time may be any time period between one day and twenty years, including, but not limited to, five years, two years, six months, three months, one month, and one week. The historical prescription data may include the total number of prescriptions filled by the healthcare provider and the total number of prescriptions filled by the healthcare provider for each class of controlled substance. Alternatively, the historical prescription data may include the total number of pills or doses filled by the healthcare provider and the total number of pills or doses of prescriptions filled by the healthcare provider for each class of controlled substance.

Table I below provides an example of the historical prescription data pulled for two healthcare providers associated with a healthcare provider chain that has requested controlled substance level monitoring, such as that which may be provided by step 315. In the table below, columns Class 2, Class 3, Class 4, and Class 5 each represent different classes of controlled substances that may be prescribed by a healthcare provider. The table may also include the name or any other type of identifier for the pharmacy or other healthcare provider chain and the NPI for each pharmacy or healthcare provider associated with the chain. The exemplary table below lists the number or prescriptions filled but could easily be modified based on the information in the database 182 to instead recite the number of pills and or doses.

TABLE I

| Chain | NPI | Class 2 | Class 3 | Class 4 | Class 5 | Total Scripts |
|---|---|---|---|---|---|---|
| ABC | 1234567891 | 24120 | 33768 | 86586 | 106164 | 482532 |
| ABC | 2345678912 | 710700 | 639648 | 533028 | 533052 | 3553548 |

In steps 320 and 325, an average is calculated from the data pulled in step 315 for each of the total number of prescriptions filled by the healthcare provider (step 320) and the total number of prescriptions filled by the healthcare provider for each class of controlled substance (step 325) over a second predetermined amount of time. In certain exemplary embodiments, the calculation is completed by the controlled substance monitoring module 180 or the service provider computer 106. The second predetermined amount of time is one month in certain exemplary embodiments. Alternatively, the second predetermined amount of time may be any time period between one day and twenty years, including, but not limited to, one year, six months, three months, two months, two weeks, and one week. In certain exemplary embodiments, the first predetermined amount of time and the second predetermined amount of time are the same. In other exemplary embodiments, the first predetermined amount of time and the second predetermined amount of time are different. For example, if the first predetermined amount of time for the data pulled in step 315 is one year, and the second predetermined amount of time for the average being calculated in steps 320 and 325 is one month, then the amounts identified in step 315 for each of the total number of prescriptions filled by the healthcare provider and the total number of prescriptions filled by the healthcare provider for each class of controlled substance may be divided by twelve. In alternative embodiments, steps 320 and 325 can be skipped altogether and the data pulled in step 315 may be used for steps that follow.

Table II below provides an example of an average of the historical prescription data pulled for two healthcare providers associated with a healthcare provider chain that has requested controlled substance level monitoring, such as that which may be provided by steps 320 and 325. In the table below, columns Class 2, Class 3, Class 4, and Class 5 each represent different classes of controlled substances that may be prescribed by a healthcare provider. The table may also include the name of the pharmacy or other healthcare provider chain and the NPI for each pharmacy or healthcare provider associated with the chain. The exemplary table below lists the number or prescriptions filled but could easily be modified based on the information in the database 182 to instead recite the number of pills and or doses.

TABLE II

| Chain | NPI | Class 2 | Class 3 | Class 4 | Class 5 | Total Scripts |
|---|---|---|---|---|---|---|
| ABC | 1234567891 | 2010 | 2814 | 7238 | 8847 | 40211 |
| ABC | 2345678912 | 59225 | 53304 | 44419 | 44421 | 296129 |

In an alternative embodiment, instead of historical data being pulled for each healthcare provider, the historical data may be pulled for each person on entity that actually prescribes the medication, such as the doctor or other medical service provider. In step 330, an initial trigger level for each class of controlled substances is determined. In one exemplary embodiment, the initial trigger level may be calculated by the controlled substance monitoring module 180 or the service provider computer 106. In one example, the initial trigger level may be a percentage of the average total scripts for each class of controlled substance as determined in steps 320 and 325. The initial trigger level may be the exact percentage, may be rounded up or down to the nearest whole percentage point, or rounded up or down to the nearest five percent. Alternatively, the initial trigger level may be a predetermined number of prescriptions filled, doses or pills (or other units of distribution) for each class of controlled substance. In yet another alternative, the initial trigger levels may be a predetermined percentage requested by the healthcare provider or the management or corporate level associated with the healthcare provider. Table III below presents an example of the initial trigger levels based on the average prescriptions filed for each class of controlled substance presented in Table II above.

TABLE III

| Chain | NPI | Class 2 | Class 3 | Class 4 | Class 5 | Total Scripts |
|---|---|---|---|---|---|---|
| ABC | 1234567891 | 5% | 7% | 18% | 22% | 40211 |
| ABC | 2345678912 | 20% | 18% | 15% | 15% | 296129 |

Once the initial trigger levels have been determined for each class of controlled substance in step 330, the process continues to the END step.

Figure 4A:
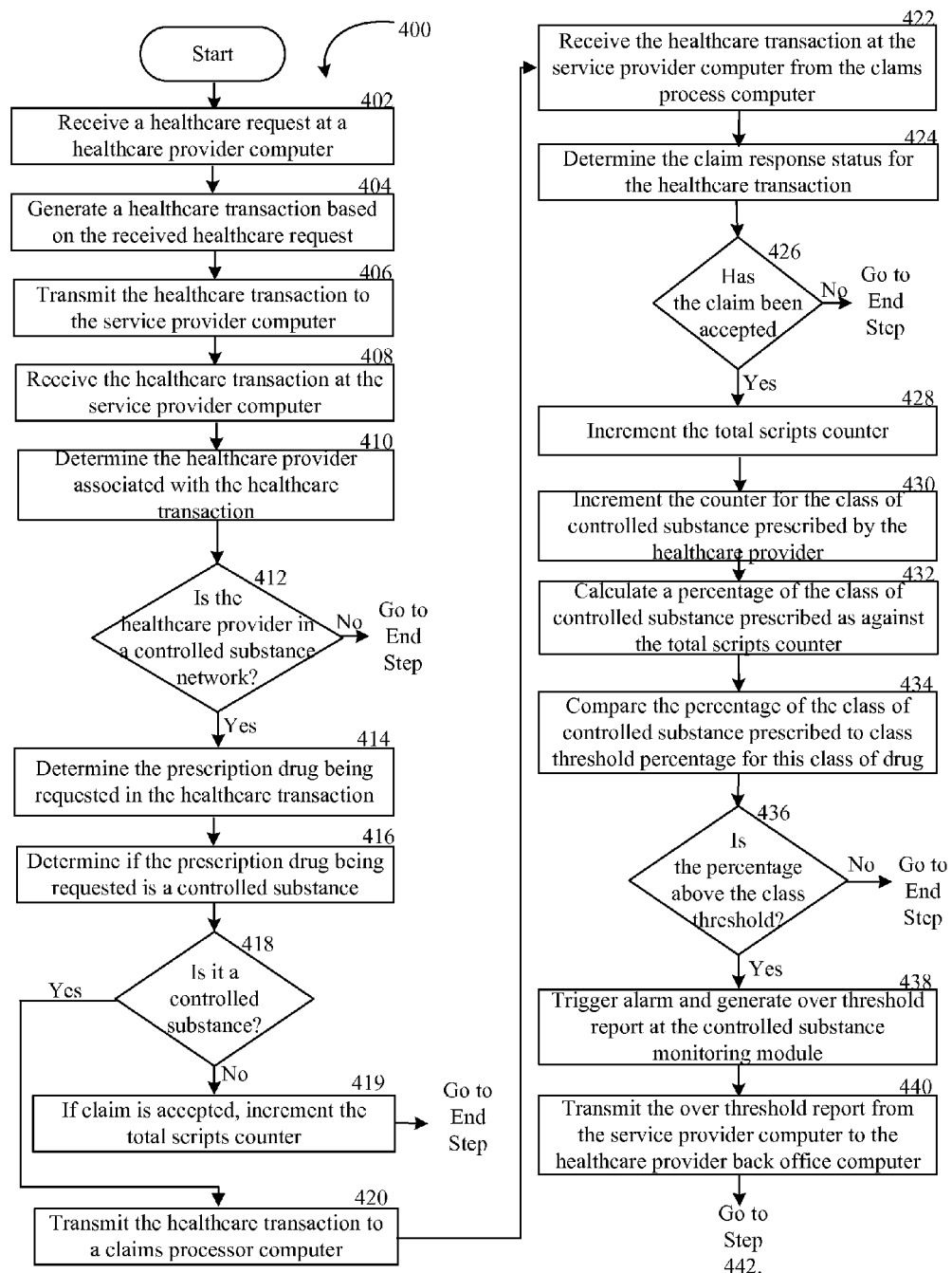
FIGS. 4A and 4B are a flow chart of an example method for monitoring the distribution levels of controlled substances by a healthcare provider as a part of the processing of a healthcare transaction, according to an illustrative embodiment of the invention.
Figure 4B:
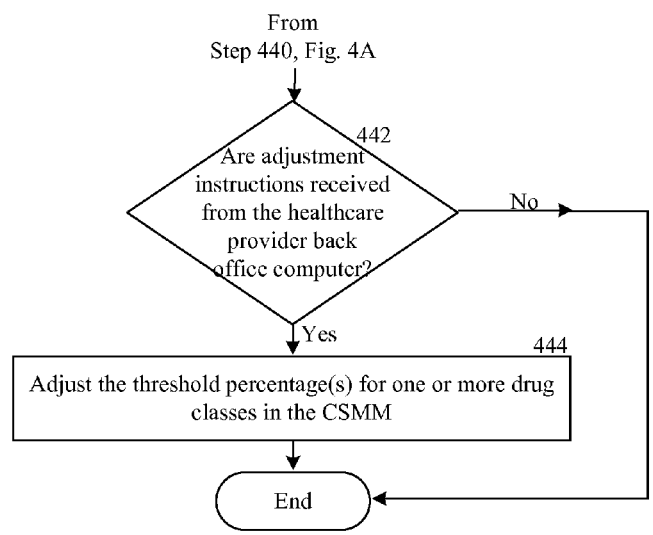

FIGS. 4A and 4B are a flow chart of an example method 400 for monitoring the distribution levels of controlled substances by a healthcare provider as a part of the processing of a healthcare transaction in accordance with one exemplary embodiment. The exemplary method 400 may be performed by a suitable service provider computer 106 and/or a controlled substance monitoring module 180. The controlled substance monitoring module 180 may be associated with the service provider computer 106, such as the service provider computer 106 and the controlled substance monitoring module 180 illustrated in FIG. 1. Alternatively, the controlled substance monitoring module may be associated with a third-party computer.

Referring now to FIGS. 1, 4A, and 4B, the exemplary method 400 begins at the START step and proceeds to step 402, where a healthcare request is received at the healthcare provider computer 104. The healthcare request may be transmitted or provided by a patient. The healthcare request may be a prescription order that is received in-person, such as at a pharmacy location or store, or electronically by phone or via one or more suitable network connections. Alternatively, a physician/clinic/hospital computer may communicate a healthcare request as an electronic prescription order (e.g. and E-SCRIPT) to the healthcare provider computer.

A healthcare transaction request (also referred to herein as a healthcare transaction) is generated based on the received healthcare request in step 404. In one exemplary embodiment, the healthcare transaction request is generated by the healthcare provider computer 104. In step 406, the healthcare provider computer 104 transmits the healthcare transaction to the service provider computer 106. In one exemplary embodiment the healthcare transaction is transmitted by way of the network 110. The healthcare transaction is received at the service provider computer 106 in step 408.

In step 410, a determination is made as to the healthcare provider associated with the healthcare transaction. In one exemplary embodiment, the determination is made by the service provider computer 106. For example, the service provider computer 106 may parse the healthcare transaction to determine a healthcare provider identifier, such as the NPI or other type of provider code. The service provider computer 106 may then compare the NPI or other type of provider code to information stored in the database 182 to determine the identity of the healthcare provider.

An inquiry is conducted in step 412 to determine if the healthcare provider identified in step 410 is in a controlled substance network. In one exemplary embodiment, the determination is made by the controlled substance monitoring module 180 and/or the service provider computer 106. In one example, the service provider computer 106 determines that the healthcare provider is in a controlled substance network if it has requested controlled substance level monitoring. As such, the service provider computer 106 may compare the identification information for the healthcare provider to a listing of entities that are receiving controlled substance level monitoring, which may be stored in the database 182. If the service provider computer 106 determines that the healthcare provider is not in a controlled substance network (e.g. there was no match between the identification information for the healthcare provider to a listing of healthcare providers that are receiving controlled substance level monitoring), the NO branch is followed to the END step. On the other hand, if the service provider computer 106 determines that the healthcare provider is in a controlled substance network (e.g. there was a match between the identification information for the healthcare provider to a listing of healthcare providers that are receiving controlled substance level monitoring), the YES branch is followed to step 414.

In step 414, the drug being prescribed in the healthcare transaction is determined. In certain exemplary embodiments, the determination is made by the controlled substance monitoring module 180 or the service provider computer 106. In one example, the determination is made by the module 180 parsing the healthcare transaction to determine an identifier for the drug being prescribed in the healthcare transaction. The identifier may be the national drug code (NDC), another code, or the actual name of the drug being prescribed. In examples where the drug is identified by an NDC or other type of code, the controlled substance monitoring module 180 or the service provider computer 106 can query the database 182 to determine the name of the drug based on the NDC or other type of code. A determination is made as to whether the drug being prescribed is a controlled substance under one of the five classes outlined by the U.S. Drug Enforcement Agency under the Controlled Substances Act in step 416. In certain exemplary embodiments, this determination is made by the controlled substance monitoring module 180 and/or the service provider computer 106. For example, once the NDC has been parsed from the healthcare transaction, the controlled substance monitoring module 180 or the service provider computer 106 may compare the NDC to records stored in the database 182. In the database 182, each NDC record can be associated with a notification if and to which class of controlled substance a drug is categorized under. Alternatively, a notification if and to which class of controlled substance a drug is categorized under can be included in the healthcare transaction and may be parsed out thereof and identified by the controlled substance monitoring module 180 and/or the service provider computer 106.

In step 418, an inquiry is conducted to determine if the drug being prescribed is a controlled substance based on the evaluation conducted in step 416. If the drug being prescribed is not a controlled substance, then the NO branch is followed to step 419. In step 419, if the healthcare transaction claim is accepted/approved by the claims processor, a total script count is incremented upward by one by the controlled substance monitoring module 180 or the service provider computer 106. In this example, the healthcare transaction is transmitted by the service provider computer 106 to the claims processor by way of the claims processor computer 108 to adjudicate or otherwise process the transaction for acceptance/approval. The claims processor via the claims processor computer 108 may then send back the healthcare transaction in the form of an adjudicated reply or response to the service provider computer 106, which may pass it, a copy, or a notification of the outcome of the adjudication (e.g. approval, denial) to the controlled substance monitoring module 180. If approved, the controlled substance monitoring module may then increase a counter for total scripts prescribed by the particular healthcare provider by one. In alternative embodiments where the total number of pills or doses is being evaluated rather than the total number of prescriptions, the controlled substance monitoring module 180 or the service provider computer 106 may also parse out the number of pills or doses the drug prescribed in the healthcare transaction and may alternatively increment the total scripts counter by the number of pills or doses being prescribed. The process then continues to the END step.

Returning to step 418, if a determination is made that the drug being prescribed is a controlled substance, then the YES branch is followed to step 420, where the healthcare transaction is transmitted to the claims processor to adjudicate or otherwise process the transaction for acceptance/approval. In certain exemplary embodiments, the healthcare transaction is transmitted by the controlled substance monitoring module 180 or the service provider computer 106 to the claims processor computer 108 via the network 110. In one example, the claims processor is determined from at least a portion of the information in the healthcare transaction that is parsed out by the service provider computer 106 or the controlled substance monitoring module 180. The healthcare transaction in the form of an adjudicated reply or response is received by the service provider computer 106 or the controlled substance monitoring module 180 from the claims processor by way of the claims processor computer 108 in step 422.

In step 424, the controlled substance monitoring module 180 and/or the service provider computer 106 determine a claim response status for the healthcare transaction. Claim response status may be approved, denied, or a request for additional information. The claim response status may be determined by the controlled substance monitoring module 180 parsing the healthcare transaction that has been modified by the claims processor, for example, by the claims processor computer 108 to determine the adjudicated reply or response. An inquiry is conducted in step 426 to determine if the prescription claim in the healthcare transaction has been accepted/approved. If the claim has not been accepted/approved, the NO branch is followed to the END step. Otherwise, the YES branch is followed to step 428, where the controlled substance monitoring module 180 or the service provider computer 106 increments a total script counter upward by one for the particular healthcare provider to create an updated total scripts count. In one exemplary embodiment, the count that is incremented is the count determined under the column Total Scripts in either of tables I and II. Alternatively, a new or different table maintaining a separate count that is incremented in step 428 is used. For example, while exemplary Table I is a representation of one year of counts (either for scripts, total doses, or total pills, whichever is desired under one of the exemplary embodiments), the table or counter for which a count is incremented in step 428 can be for a different historical time period (such as the prior six months (or any other time period between one day-twenty years) and then going forward). In one example the total script counter for the particular healthcare provider is maintained in the database 182 and is accessed and updated by the module 180.

In step 430, the counter for the particular class of drug being prescribed for the particular healthcare provider is incremented by one to create an updated controlled class count. In one exemplary embodiment, the count that is incremented is the count determined under one of columns Class 1, Class 2, Class 3, Class 4, and/or Class 5 (additional or fewer classes may be monitored and incremented) in either of tables I and II. Alternatively, a new or different table maintaining a separate count for each of the classes that are incremented in step 430 is used. For example, while exemplary Table I is a representation of one year of counts for multiple classes (either for total scripts, total doses, or total pills, whichever is desired under one of the exemplary embodiments), the table or counter for which a count is incremented in step 430 can be for a different historical time period (such as the prior six months (or any other time period between one day-twenty years) and then going forward). In one example the total script counter for the particular healthcare provider is maintained in the database 182 and is accessed and updated by the module 180. In certain exemplary embodiments, the counters for each of the classes of controlled substances that have been prescribed by each of the healthcare providers are maintained in the database 182 and accessed and updated by the module 180. The particular class of controlled substance being prescribed can be determined similar to that described with regard to step 418 by the module 180 or the service provider computer 106. Similar to that discussed earlier, in the example of steps 428 and 430, the count represents the number of prescriptions being filled (i.e. total scripts filled for all prescriptions or for a particular class). Alternatively, the count may be modified to represent and count the total number of pills or doses that are filled for all prescriptions and for each class of controlled substances as this information is already included in the healthcare transaction and can be parsed and identified from the healthcare transaction by the service provider computer 106 and/or the controlled substance monitoring module 180.

In step 432, the current percentage for the class of drug being prescribed in the healthcare transaction is calculated. In certain examples, the current percentage is calculated by the controlled substance monitoring module 180 or the service provider computer 106 by dividing the updated controlled class count determined in step 430 by the updated total scripts count determined in step 428. The current percentage for the particular class of controlled substance for the particular healthcare provider in the healthcare transaction is compared to the predetermined class threshold percentage (or trigger level) for this class of controlled substance for this particular healthcare provider in step 434. In one example, the comparison is made by the controlled substance monitoring module 180 or the service provider computer 106. In certain exemplary embodiments, the predetermined class threshold percentage (or trigger level is determined as described in step 330 of FIG. 3.

An inquiry is conducted to determine if the current percentage for the class of controlled substance for the particular healthcare provider is greater than the predetermined class threshold level for the particular class of controlled substance in step 436. Alternatively, in step 436, the inquiry may be as to whether the current percentage is greater than or equal to the predetermined class threshold level for the particular class of controlled substance. If the current percentage is not greater than (in one example) or greater than or equal to (in an alternative example) the predetermined class threshold level, the NO branch is followed to the END step. However, if the current percentage is greater than (in one example) or greater than or equal to (in the alternative example) the predetermined class threshold level, the YES branch is followed to step 438.

In step 438, a trigger alarm may be generated and a notification of over threshold report may be generated at the controlled substance monitoring module 180 or the service provider computer 106. The notification of over threshold report may include the name, location, and NPI for the particular healthcare provider, the class of controlled substance for which the threshold has been exceeded (in one example) or met or exceeded (in an alternative example), the current percentage prescribed for the particular class of controlled substance, the predetermined threshold level for the particular class of controlled substance, the updated controlled class count, the updated total script count and/or the contact information setting forth the person, location, and/or email address that the notification should be sent. Each of these parameters may be stored and updated in the database 182 by either the controlled substance monitoring module or the service provider module 106.

The notification of over threshold report is transmitted in step 440. In one example the notification may be transmitted by the controlled substance monitoring module 180 to the healthcare provider back office computer 195 via the network 110. Alternatively, the notification may be transmitted by the service provider computer 106 to the healthcare provider back office computer 195 via the network 110. In another alternative embodiment, the notification may be sent by either the module 180 or the service provider computer 106 to the particular healthcare provider by way of the healthcare provider computer 104 instead of or in combination with the transmission to the healthcare provider back office computer 195.

Once the notification is sent by the service provider, either by way of the module 180 or the service provider computer 106, the healthcare provider may determine how it wants to respond to the situation. For example, based on the information provided in the notification, the corporate level of the healthcare provider or chain to which the healthcare provider is affiliated may investigate the particular healthcare provider to determine why the predetermined threshold levels for a class of controlled substance are being exceeded. Alternatively, or after completing an investigation, the healthcare provider may determine that the predetermined threshold level for this or other classes of controlled substances for the particular healthcare provider needs to be increased due to any number of potential factors including, but not limited to, the introduction of one or more new drugs into the particular class of controlled substance for which the predetermined threshold was exceeded, a change has occurred over time in demographics for the area the healthcare provider is located, additional physicians or medical practices have moved into the area thereby increasing the number of parties potentially prescribing controlled substances as a part of their medical practice, a reduction in the number of competing healthcare providers in the area, other factors changing, and the like.

In step 442, an inquiry is conducted to determine if adjustment instructions are received from the healthcare provider. The adjustment instructions may be transmitted from the healthcare provider back office computer 195 or the healthcare provider computer 104 and may be received by the service provider computer 106 or the controlled substance monitoring module 180. The adjustment instructions may include a request to increase, decrease or maintain at the same level one or more of the predetermined threshold percentages, dose counts or pill counts (whichever is being used for the threshold triggers) for classes of controlled substances for a particular healthcare provider. If no adjustment instructions are received by the module 180 or the service provider computer 106, the NO branch is followed to the end step. Alternatively, if adjustment instructions are received, the YES branch is followed to step 444, where one or more threshold percentages for a particular class of controlled substance for a particular healthcare provider may be updated. For example, depending on the type of instructions, the module 180 or the service provider computer 106 may parse the adjustment instructions and change the predetermined threshold percentage stored for one or more classes of controlled substances for the particular healthcare provider in the database 182. The process then continues to the END step.

The operations described and shown in the methods 300 and 400 of FIGS. 3-4B may be carried out or performed in any suitable order as desired in various embodiments of the invention. Additionally, in certain exemplary embodiments, at least a portion of the operations may be carried out in parallel. Furthermore, in certain exemplary embodiments, less than or more than the operations described in FIGS. 3-4B may be performed.

Accordingly, example embodiments of the invention can provide the technical effects of creating a system and method that provides real-time controlled substance level prescription monitoring at the healthcare provider level for chains or organization that are responsible for or associated with multiple healthcare providers. In this regard, situations in which a particular healthcare provider may be prescribing an unusually high percentage or number of one or more classes of controlled substances can be identified to ensure there is not fraud or other malfeasance associated with the prescription practices of the particular healthcare provider.

Various block and/or flow diagrams of systems and methods and/or computer program products according to example embodiments of the invention are described above. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a special purpose computer or other particular machine, a processor, or other programmable data processing apparatus to produce a particular machine, such that the instructions that execute on the computer, processor, or other programmable data processing apparatus create means for implementing one or more functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer usable medium having a computer readable program code or program instructions embodied therein, said computer readable program code adapted to be executed to implement one or more functions specified in the flow diagram step or steps. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram step or steps.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special purpose hardware and computer instructions.

Many modifications and other embodiments of the invention set forth herein will be apparent having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A computer-implemented method, comprising:
receiving, from a healthcare provider computer associated with a healthcare provider, a healthcare transaction comprising one or more prescriptions for a patient, the one or more prescriptions comprising at least one controlled substance;
determining, based at least in part on information included in the healthcare transaction, a class of controlled substance to which each controlled substance identified in the healthcare transaction belongs, wherein the class of controlled substance is one of Schedule I, II, III, or IV, as defined by the U.S. Food and Drug Administration;
determining a current percentage of distribution by the healthcare provider for the class of controlled substance being prescribed by dividing a number of prescriptions issued for each class of controlled substance over a predetermined amount of time by a total number of prescriptions issued by the healthcare provider over the predetermined amount of time;
comparing the current percentage of distribution to a predetermined threshold percentage of distribution for the class of controlled substance being prescribed;
determining if the current percentage violates the predetermined threshold percentage of distribution for the class of controlled substance being prescribed; and
transmitting a notification to the healthcare provider based on a positive determination that the current percentage violates the predetermined threshold percentage,
wherein the above operations are performed by one or more computers associated with a service provider.

2. The computer-implemented method of claim 1, wherein the current percentage violates the predetermined threshold percentage if the current percentage is greater than the predetermined threshold percentage.

3. The computer-implemented method of claim 1, wherein the current percentage violates the predetermined threshold percentage if the current percentage is greater than or equal to the predetermined threshold percentage.

4. The computer-implemented method of claim 1 further comprising the step of determining for the healthcare provider with one or more computers associated with a service provider a predetermined threshold percentage for each of a plurality of classes of controlled substances.

5. The computer-implemented method of claim 4, wherein determining for the healthcare provider the predetermined threshold percentage for each of a plurality of classes of controlled substances comprises the steps of:
receiving a plurality of historical healthcare transaction data for the healthcare provider for a first predetermined amount of time;
determining, based at least in part on information included in the historical healthcare transaction data, a total number of prescriptions filled by the healthcare provider during the first predetermined amount of time;
determining for each of a plurality of classes of controlled substances, based at least in part on information included in the historical healthcare transaction data, a number of class prescriptions filled by the healthcare provider during the first predetermined amount of time; and
calculating for each of the plurality of classes of controlled substances, the predetermined threshold percentage.

6. The computer implemented method of claim 5, wherein calculating for each of the plurality of classes of controlled substances, the predetermined threshold percentage comprises the steps of:
calculating an average number total number of prescriptions filled by the healthcare provider during a second predetermined amount of time;
calculating for each of the plurality of classes of controlled substances, an average number of class prescriptions filled by the healthcare provider during the second predetermined amount of time; and
calculating for each of the plurality of classes of controlled substances the predetermined threshold percentage by dividing the average number of class prescriptions filled by the average number total prescriptions filled by the healthcare provider,
wherein the above operations are performed by one or more computers associated with a service provider.

7. The computer-implemented method of claim 6, wherein the second predetermined amount of time is a subset of the first predetermined amount of time.

8. The computer-implemented method of claim 1, wherein determining a current percentage of distribution by the healthcare provider for the class of controlled substance being provided comprises the steps of:
incrementing a total prescription count by one for the healthcare provider;
incrementing a controlled class count by one for the class of controlled substance for the healthcare provider; and
calculating the current percentage by dividing the controlled class count for the class of controlled substance by the total prescription count.

9. The computer-implemented method of claim 8, further comprising the steps of:
receiving from a claims processor computer a claim response status for the healthcare transaction;
determining, at least in part from the claim response status for the healthcare transaction, if the healthcare transaction has been approved; and
incrementing the total prescription count based on a positive determination that the healthcare transaction has been approved.

10. The computer-implemented method of claim 1, wherein the notification comprises:
an identifier for the healthcare provider;
the class of controlled substance for which the predetermined threshold percentage has been violated;
the current percentage of distribution for the class of controlled substance for the healthcare provider; and
the predetermined threshold percentage for the class of controlled substance for the healthcare provider.

11. The computer-implemented method of claim 1, wherein transmitting the notification to the healthcare provider comprises:
determining a healthcare provider back office computer associated with the healthcare provider; and
transmitting the notification to the healthcare provider back office computer.

12. A system, comprising;
at least one memory operable to store computer-executable instructions; and
at least one processor configured to access the at least one memory and execute the computer-executable instructions to:

receive, from a healthcare provider computer associated with a healthcare provider, a healthcare transaction comprising one or more prescriptions for a patient, the one or more prescriptions comprising at least one controlled substance;

determine, based at least in part on information included in the healthcare transaction, a class of controlled substance to which each controlled substance identified in the healthcare transaction belongs, wherein the class of controlled substance is one of Schedule I, II, III, or IV, as defined by the U.S. Food and Drug Administration;

determine a current percentage of distribution by the healthcare provider for the class of controlled substance being prescribed by dividing a number of prescriptions issued for each class of controlled substance over a predetermined amount of time by a total number of prescriptions issued by the healthcare provider over the predetermined amount of time;

compare the current percentage of distribution to a predetermined threshold percentage of distribution for the class of controlled substance being prescribed;

determine if the current percentage violates the predetermined threshold percentage of distribution for the class of controlled substance being prescribed; and direct the communication of a notification to the healthcare provider computer based on a positive determination that the current percentage violates the predetermined threshold percentage.

13. The system of claim 12, wherein the at least one processor is further configured to determine for the healthcare provider a predetermined threshold percentage for each of a plurality of classes of controlled substances.

14. The system of claim 13, wherein the at least one processor is further configured to determine for the healthcare provider a predetermined threshold percentage for each of a plurality of classes of controlled substances by executing computer-executable instructions to:

receive a plurality of historical healthcare transaction data for the healthcare provider for a first predetermined amount of time;

determine, based at least in part on information included in the historical healthcare transaction data, a total number of prescriptions filled by the healthcare provider during the first predetermined amount of time;

determine for each of a plurality of classes of controlled substances, based at least in part on information included in the historical healthcare transaction data, a number of class prescriptions filled by the healthcare provider during the first predetermined amount of time; and calculate for each of the plurality of classes of controlled substances, the predetermined threshold percentage.

15. The system of claim 14, wherein the at least one processor is configured to calculate for each of the plurality of classes of controlled substances, the predetermined threshold percentage by accessing the at least one memory and executing computer-executable instructions to:

calculate an average total number of prescriptions filled by the healthcare provider during a second predetermined amount of time;

calculate for each of the plurality of classes of controlled substances, an average number of class prescriptions filled by the healthcare provider during the second predetermined amount of time; and calculate for each of the plurality of classes of controlled substances the predetermined threshold percentage by dividing the average number of class prescriptions filled by the average number total prescriptions filled by the healthcare provider.

16. The system of claim 12, wherein the at least one processor is configured to determine a current percentage of distribution by the healthcare provider for the class of controlled substance being provided by accessing the at least one memory and executing computer-executable instructions to:

increment a total prescriptions count by one for the healthcare provider;

increment a controlled class count by one for the class of controlled substance for the healthcare provider; and calculate the current percentage by dividing the controlled class count for the class of controlled substance by the total prescriptions count.

17. The system of claim 12, wherein the at least one processor is configured to direct the communication of the notification to the healthcare provider by accessing the at least one memory and executing computer-executable instructions to:

determine a healthcare provider back office computer associated with the healthcare provider; and direct communication of the notification to the healthcare provider back office computer.

18. The system of claim 12, wherein the current percentage violates the predetermined threshold percentage if the current percentage is greater than the predetermined threshold percentage.

19. The system of claim 12, wherein the current percentage violates the predetermined threshold percentage if the current percentage is greater than or equal to the predetermined threshold percentage.

20. The system of claim 12, wherein the notification comprises:

an identifier for the healthcare provider;

the class of controlled substance for which the predetermined threshold percentage has been violated;

the current percentage of distribution for the class of controlled substance for the healthcare provider; and the predetermined threshold percentage for the class of controlled substance for the healthcare provider.

* * * * *